US012564499B2

(12) United States Patent
Terziotti et al.

(10) Patent No.: US 12,564,499 B2
(45) Date of Patent: Mar. 3, 2026

(54) UNIBODY ORTHOPEDIC SURGICAL INSTRUMENT

(71) Applicant: Joint Development, Inc., Salt Lake City, UT (US)

(72) Inventors: Luca Terziotti, Salt Lake City, UT (US); Eric M Dacus, Salt Lake City, UT (US); Nabil M. Rizk, Salt Lake City, UT (US); Dermott J. McHugh, Salt Lake City, UT (US)

(73) Assignee: Joint Development, Inc., Salt Lake City, UT (US)

( * ) Notice: Subject to any disclaimer, the term of this patent is extended or adjusted under 35 U.S.C. 154(b) by 603 days.

(21) Appl. No.: 17/978,039

(22) Filed: Oct. 31, 2022

(65) Prior Publication Data

US 2023/0139676 A1 May 4, 2023

Related U.S. Application Data

(60) Provisional application No. 63/273,781, filed on Oct. 29, 2021.

(51) Int. Cl.
*A61F 2/46* (2006.01)
*A61B 17/88* (2006.01)
*A61F 2/38* (2006.01)

(52) U.S. Cl.
CPC ............ *A61F 2/461* (2013.01); *A61F 2/4684* (2013.01); *A61B 17/88* (2013.01); *A61F 2/389* (2013.01)

(58) Field of Classification Search
CPC .............. A61F 2/461; A61F 2002/4622; A61F 2002/4625; A61F 2002/4628
See application file for complete search history.

(56) References Cited

U.S. PATENT DOCUMENTS

| | | | | | |
|---|---|---|---|---|---|
| 3,215,006 A | * | 11/1965 | Urani | ................. | H01H 85/0208 81/3.8 |
| 3,654,824 A | * | 4/1972 | Reed | ................... | B25B 27/0035 81/3.8 |
| 3,817,078 A | * | 6/1974 | Reed | .................... | A61B 17/076 29/426.6 |
| 4,079,765 A | * | 3/1978 | Hatayan | ................. | B25C 3/008 24/457 |
| 4,226,459 A | * | 10/1980 | Natalicio | ................. | B25B 9/02 294/99.2 |
| 4,841,819 A | * | 6/1989 | Williams | ............ | B25B 27/0035 81/3.8 |
| 5,387,019 A | * | 2/1995 | Britzke | .................... | B25B 9/02 294/99.2 |

(Continued)

*Primary Examiner* — Nicholas W Woodall
(74) *Attorney, Agent, or Firm* — Lowry Blixseth APC; Scott M. Lowry

(57) ABSTRACT

The unibody orthopedic instrument includes an elongated handle, a latching interface outwardly extending relative to the elongated handle and selectively couplable to an orthopedic component, and a hand accessible spring-biased lever arm operable with a hinge coupled to the elongated handle about a pivot. The hinge normally positions the latching interface in a first latched position for locking engagement with the orthopedic component and is otherwise operable by the spring-biased lever arm about the pivot to reposition the latching interface from the normally latched position to an unlatched position for disengagement from the orthopedic component.

24 Claims, 12 Drawing Sheets

(56)            References Cited

U.S. PATENT DOCUMENTS

| 5,797,298 | A  * | 8/1998 | Grevel | ................. | H01R 13/443 |
| | | | | | 81/3.8 |
| 7,384,086 | B2 * | 6/2008 | Lukaszynski | ...... | H01H 85/0208 |
| | | | | | 81/3.8 |
| 9,636,236 | B2 * | 5/2017 | Anderson | ............. | A61F 2/4606 |
| 2023/0139676 | A1 * | 5/2023 | Terziotti | ................ | A61F 2/4684 |
| | | | | | 606/102 |

\* cited by examiner

UNIBODY ORTHOPEDIC SURGICAL INSTRUMENT

BACKGROUND OF THE INVENTION

The present invention generally relates to a unibody orthopedic surgical instrument. More specifically, the unibody orthopedic surgical instrument includes a body-integrated actuator operable to actuate a hinge that selectively opens a latching interface of a size and shape for select engagement with an orthopedic implant.

During knee arthroplasty, the proximal end of a patient tibia is resurfaced before affixing a knee replacement tibial baseplate to the bone and seating a tibial insert on the tibial baseplate. Resurfacing the proximal end of the tibia requires resecting the damaged portion of bone and cartilage to create a substantially flat surface for the tibial baseplate. Prior to affixing the tibial baseplate, a surgeon aligns a tibial trial generally following the peripheral edge of the resurfaced tibia to determine the size of the requisite tibial baseplate. This may require aligning incrementally sized tibial trials until the correct size is ascertained. Furthermore, the size of tibial insert is determined by a similar process using insert trials. The tibial insert is located between the tibial baseplate and a femoral component affixed to the distal end of a patient femur. The circumference of the tibial insert must match the tibial baseplate, and the height of the tibial insert must fit within the gap between the femoral component and tibial baseplate. As such, determining the correct sized tibial insert may require aligning incrementally sized insert trials.

Typically, the tibial trials, insert trials, and/or tibial sizers include integrated handles. Therefore, each incrementally sized trial or sizer with an integrated handle is unnecessarily large because the trials or sizers each have their own handle, as opposed to being adapted for use with a universal handle. Furthermore, knee arthroplasty generally utilizes surgical trays containing the trials, implant components, sizers, and surgical instruments. To accommodate large trials or sizers with integrated handles, the surgical trays are unnecessarily large, which is burdensome and undesirable for already crowded operating rooms. Furthermore, the surgical trays have mass constraints and, therefore, unnecessarily large trials or sizers can require multiple trays. This further crowds the operating room and creates an inconvenient procedural environment. Additionally, the cost of sterilizing the trials, implant components, sizers, and multiple surgical instruments can be undesirable. Therefore, the current practice for determining the size of the required tibial baseplate and insert is time-consuming, inconvenient, and costly.

Furthermore, the tibial baseplate includes a stem that extends into the patient tibia and anchors the baseplate to the bone. The tibial baseplate stem may need to be tightened or loosened to adjust the length of the stem depending on the size of the patient tibia and type of knee replacement being inserted. Alternatively, stems of varying lengths may be coupled or removed from the tibial baseplate. In either scenario, a stem wrench is used to tighten, loosen, couple, or remove the stem. Typically, this requires a separate stem wrench. Conventional practices, therefore, require that even more individual surgical devices be delivered and used in the operating room during surgery.

Current attempts to reduce the number of individual devices used for knee arthroplasty have been largely unsuccessful in satisfying the need and, in some cases, create additional problems. In one example prior art device, U.S. Pat. No. 5,733,290, the contents of which are herein incorporated by reference in its entirety, discloses a quick-release alignment handle system that includes a quick release mechanism with an attachable releasable lock for attaching the handle to a tibial tray trial component of a surgical instrument system for implanting artificial knees. While this device includes a handle that may couple to multiple tibial trials, it does not couple to insert trials or any other surgical instrument. Furthermore, existing devices include complicated mechanisms containing springs, sliding components, and/or multi-piece assemblies. As such, existing devices are more susceptible to wear and have more potential failure points relative to a unibody device. Another drawback of these complicated mechanisms is that they are more difficult to manufacture and assemble, thereby increasing costs. Additionally, any surgical instrument used during the procedure must be thoroughly cleaned and resterilized before use in subsequent procedures. This is more difficult with existing devices because the springs, sliding components, and/or multi-piece assemblies are prone to collect debris in areas difficult to clean. This consequently increases hospital reprocessing time and also adds to costs. Additional, current devices fail to incorporate a stem wrench and, therefore, conventional surgical instruments still require that multiple sterilized instruments be delivered to the operating room for any given surgery.

There exists, therefore, a significant need in the art for a unibody orthopedic surgical instrument that includes a body-integrated actuator operable to actuate a hinge that opens a latching interface of a size and shape for select pull-tight engagement with an orthopedic instrument, the unibody surgical instrument further including a body-integrated alignment rod aperture and a tibial stem wrench, thereby combining multiple operating room surgical instrument tools into one. The present invention fulfills these needs and provides further related advantages.

SUMMARY OF THE INVENTION

In accordance with one embodiment, a unibody orthopedic surgical instrument may include a handle, a latching interface outwardly extending from the handle, a hinge operably coupled with the latching interface, and a spring-biased lever arm coupled to the hinge in a configuration to actuate the latching interface. The handle may further include an alignment rod and a tibial stem wrench, thereby combining multiple surgical instruments into one.

Alternatively, in other embodiments, the unibody orthopedic instrument may include an elongated handle, a latching interface outwardly extending relative to the elongated handle and selectively couplable to an orthopedic component, and a hand accessible spring-biased lever arm operable with a hinge coupled to the elongated handle about a pivot. The hinge normally positions the latching interface in a first latched position for locking engagement with the orthopedic component and is otherwise operable by the spring-biased lever arm about the pivot to reposition the latching interface from the normally latched position to an unlatched position for disengagement from the orthopedic component.

In one embodiment, the spring-biased lever arm may turn about and extend away from the hinge in an offset position relative thereto. Alternatively, the spring-biased lever arm may orthogonally extend out and away from the hinge; or the spring-biased lever arm may extend out relative to the hinge at an angle relative to the hinge or the elongated handle. In some embodiments, the elongated handle may further include an aperture having a size and shape for select sliding engagement with an alignment rod and/or the elongated handle may further include a body-integrated tibial stem wrench. More specifically, the aperture may include an alignment rod lock movable between a free moving position permitting movement of the unibody orthopedic instrument relative to the alignment rod and a restricted position in friction fit engagement with the alignment rod to inhibit movement of the unibody orthopedic instrument relative to the alignment rod.

The unibody orthopedic instrument may further include a lock movable relative to an operable end of the spring-biased lever arm between an unlocked position allowing the movement of the operable end of the spring-biased lever arm and a locked position obstructing movement of the operable end of the spring-biased lever arm. Here, the lock may include a rod movable within a channel separating the operable end of the spring-biased lever arm and the elongated body between the unlocked position and the locked position. The elongated handle may further include a stop that projects into the channel to locate the lock underneath the spring-biased lever arm in the locked position. Additionally, the spring-biased lever arm may terminate in a C-shaped enclosure generally encompassing an end stop outwardly projecting from the elongated handle. Here, the spring-biased lever arm may be deflectable relative to the elongated handle by a distance formed between opposing sides of the C-shaped channel.

Additionally, the latching interface may include a pair of pretensioned prongs positioned relatively closer to one another when in the latched position than when in the unlatched position. One of the pair of pretensioned prongs may include a chamfered prong having a chamfered leading edge and the other of the pair of pretensions prongs may include a hooked prong having a notch formed thereunder. Accordingly, the latching interface may be of a size and shape for select slide-in reception within a pair of receptors integrated into the orthopedic component for locking engagement therewith. Once connected thereto, the unibody orthopedic instrument may manipulate the orthopedic component, such as during surgery.

In an alternative embodiment, the unibody orthopedic instrument may include a handle, a latching interface outwardly extending relative to the handle and selectively couplable to an orthopedic component, and a spring-biased lever arm integrated with a hinge coupled to the handle about a pivot normally positioning the latching interface in a first latched position for locking engagement with the orthopedic component. Here, the hinge may be operable by the spring-biased lever arm about the pivot to reposition the latching interface from the normally latched position to an unlatched position for disengagement from the orthopedic component. Moreover, a lock may be movable relative to the spring-biased lever arm between an unlocked position allowing movement of the spring-biased lever arm and a locked position obstructing movement of the spring-biased lever arm. The spring-biased lever arm may alternatively orthogonally extend out and away from the hinge or turn about and extend over the hinge in spaced-apart relation thereof.

In some embodiments, the latching interface may include a pair of pretensioned prongs positioned relatively closer to one another when in the latched position than when in the unlatched position. Additionally, the pair of pretensioned prongs may be of a size and shape for select slide-in reception within a pair of receptors integrated into the orthopedic component for locking engagement therewith. Here, one of the pair of pretensioned prongs may include a chamfered prong having a chamfered leading edge and the other of the pair of pretensioned prongs may include a hooked prong having a notch formed thereunder. The chamfered leading edge may facilitate self-actuation of the latching interface when coupling the unibody orthopedic instrument with the receiving interface of the orthopedic component.

Furthermore, in alternative embodiments, the lock may be a rod movable within a channel separating an operable end of the spring-biased lever arm and the handle. Here, the rod may be in the locked position when underneath at least a portion of the operable end of the spring-biased lever arm adjacent a stop projecting into the channel. The spring-biased lever arm may terminate in a C-shaped enclosure generally encompassing at least a portion of the handle. This allows the spring-biased lever arm to float relative to the handle by a distance of the C-shaped enclosure. Moreover, the handle may further include an aperture having a size and shape for select sliding engagement with an alignment rod and the handle may include a body-integrated tibial stem wrench. Here, the aperture may include a locking mechanism that allows the handle to lock to the alignment rod at a desired position along the length thereof. In one embodiment, the locking mechanism may be a brake-style locking mechanism that engages the alignment rod by friction fit engagement. Moreover, the body-integrated tibial stem wrench may include one or more indents (e.g., six) that correspond with one or more ribs (e.g., six) on the tibial stem to enhance engagement therewith. The handle may be ergonomically shaped, and the unibody orthopedic surgical instrument may be made out of a metal such as stainless steel, titanium, aluminum or the like.

The latching interface may couple to a tibial trial, insert trial, tibial cutting guide, or any other suitable knee arthroplasty component via the corresponding reception interface. The latching interface may include a pair of prongs, with a first prong being a chamfered prong relatively longer than a second prong being a hooked prong. The reception interface may include a pair of reception channels respectively configured for select-slide in engagement of the first prong and the second prong. The reception channels may transition to a relatively wider back channel forming a pair of shoulders therebetween. Here, a chamfered leading edge of the first prong may facilitate slide-in mating with a first recess and one of the shoulders formed within the back channel; and a latch and notch combination of the second prong may facilitate slide-in mating with a second recess and another shoulder formed within the back channel. Here, the latch and the notch may improve coupling of the prongs to the tibial trial, insert trial, tibial cutting guide, or any other suitable knee arthroplasty component.

In another aspect of the embodiments disclosed herein, a process for engaging an orthopedic component with a unibody orthopedic instrument as disclosed herein may include steps for moving a hinge operable by a spring-biased lever arm about a pivot from a normal latched position to an unlatched position, actuating a latching interface at least partially coupled with the hinge in response to movement of the hinge about the pivot, inserting the latching interface into a reception interface coupled with the orthopedic component, and returning the hinge to the normal latched position thereby locking the unibody orthopedic instrument to the orthopedic component.

In some embodiments, the actuating step may include separating a pair of pretensioned prongs. Here, a chamfered edge of one of the pair of pretensioned prongs may slide into engagement with at least one reception channel of the reception interface of the orthopedic component. The returning step may accordingly include the step of engaging at least one of the pair of pretensioned prongs having a hook and recess with a shoulder within a back channel of the reception interface. Alternatively, the spring-biased lever arm may be locked in the normal latched position by sliding a lock positioned within a channel formed between the spring-biased lever arm and a body of the unibody orthopedic instrument to a stop upwardly projecting within the channel and generally positioned underneath an operable end of the spring-biased lever arm. Moreover, the process disclosed herein may further include inserting an alignment rod into an aperture integrated within the unibody orthopedic instrument and retaining the alignment rod relative to the unibody orthopedic instrument; and turning a tibial stem via a body-integrated tibial stem wrench formed from a portion of the unibody orthopedic instrument.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
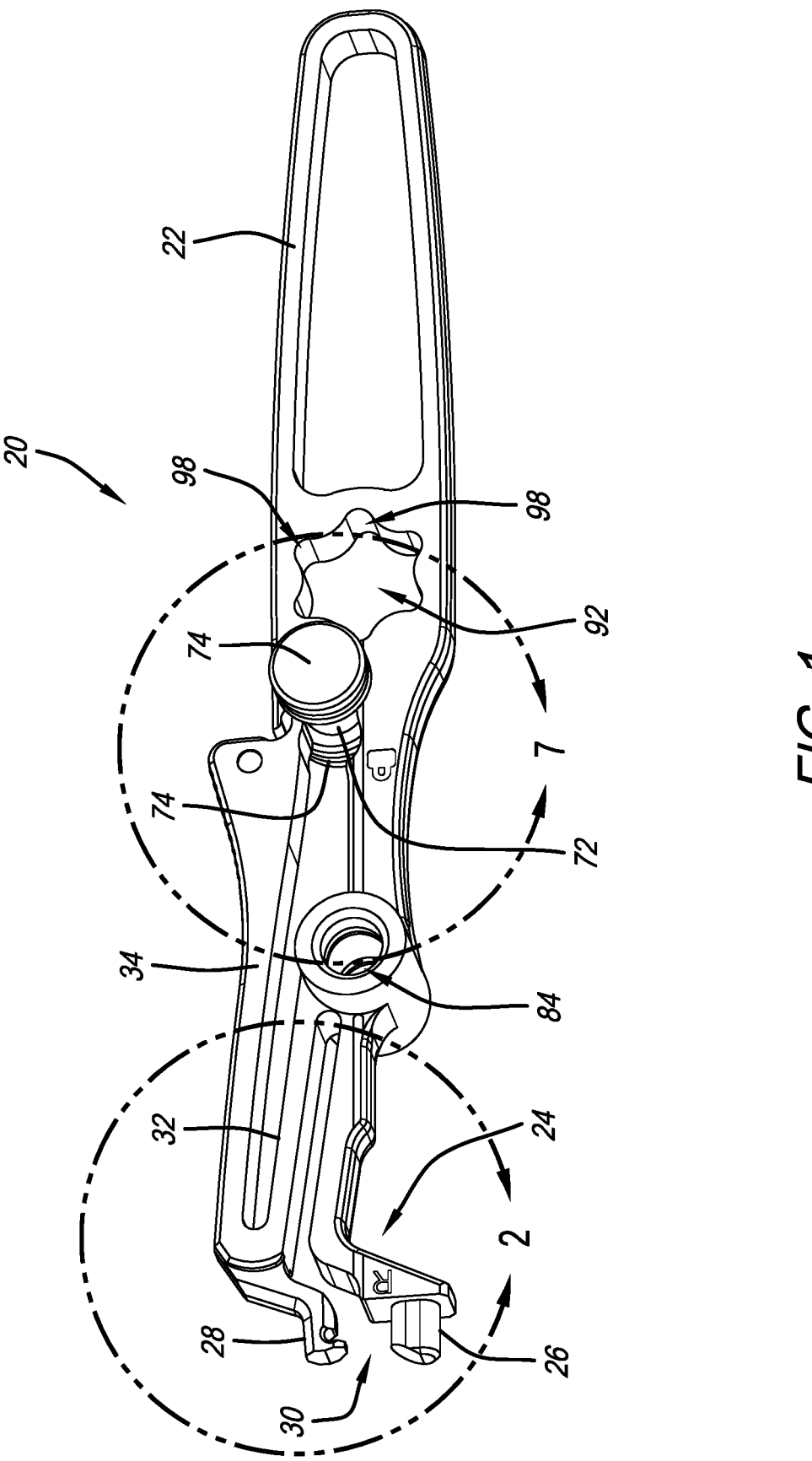
FIG. 1 is a is a perspective view of an exemplary embodiment of a unibody orthopedic surgical instrument as disclosed herein.

As shown in the exemplary drawings for purposes of illustration, the present invention for a unibody orthopedic surgical instrument is illustrated in FIGS. 1, 6, and 8-12 with respect to reference numeral 20. As illustrated, the unibody orthopedic surgical instrument 20 includes an integrated handle 22 at one end and a latching interface 24 having a pair of prongs 26, 28 generally outwardly extending therefrom at an opposite end thereof, wherein each of the pair of prongs 26, 28 are separated by a gap 30. The pair of prongs 26, 28 may include a chamfered prong 26 and a hooked prong 28 designed for select engagement with a medical device, as discussed in more detail below. In alternative embodiments, the latching interface 24 may include three or more prongs; or just a single prong as long as there is sufficient latching between components. Moreover, the unibody orthopedic surgical instrument 20 may further include a hinge 32 also formed from a portion of the integrated handle 22, the hinge 32 being operably coupled with the hooked prong 28. Although, of course, the hinge 32 could also be operably coupled with the chamfered prong 26 in the alternative. A spring-biased lever 34 arm selectively actuates the hinge 32 to increase the width of the gap 30, thereby spreading apart the chamfered prong 26 and hooked prong 28. The spring-biased lever arm 34 may generally hold the chamfered prong 26 and hooked prong 28 in a pretensioned closed position wherein the prongs 26, 28 are relatively closer together as compared to an open position when a surgeon depresses the spring-biased lever arm 34 toward the hinge 32, thereby actuating the hinge 32 to spread apart the prongs 26, 28 as disclosed herein.

Figure 2:
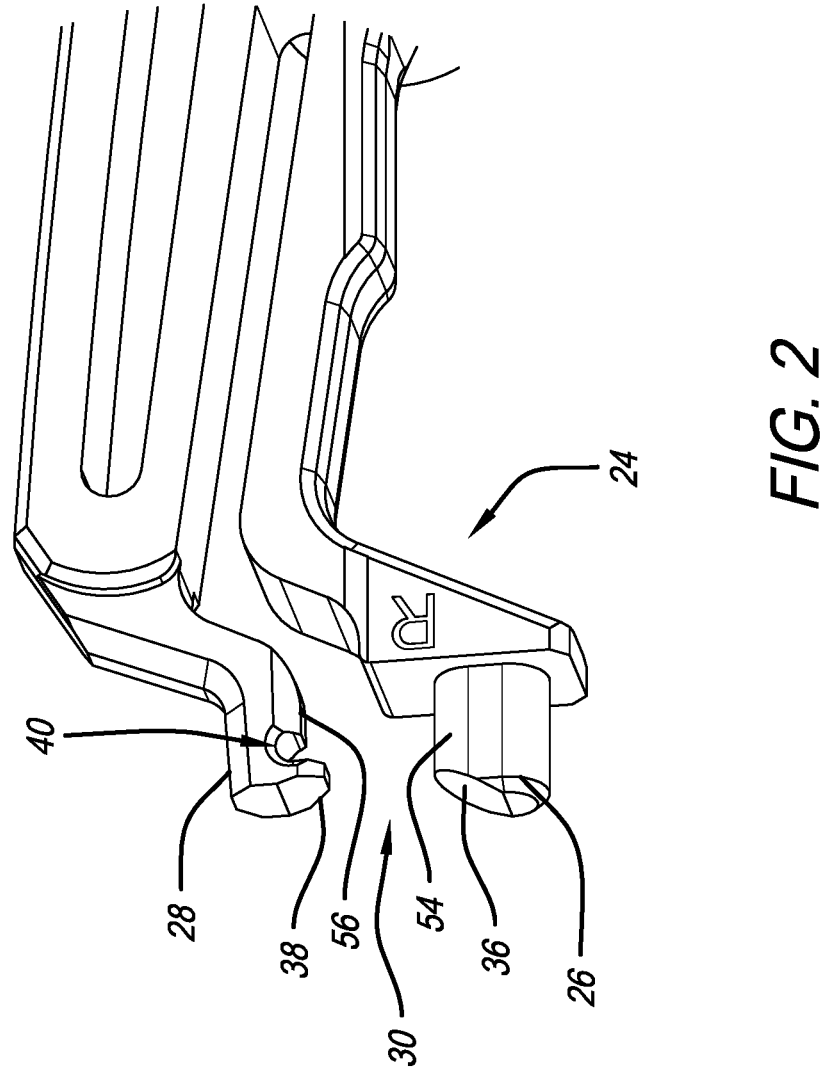
FIG. 2 is an enlarged perspective view taken about the circle 2 in FIG. 1, further illustrating that one of a pair of prongs includes a chamfered edge and that the other of the pair of prongs includes a combination latch and notch.
Figure 3:
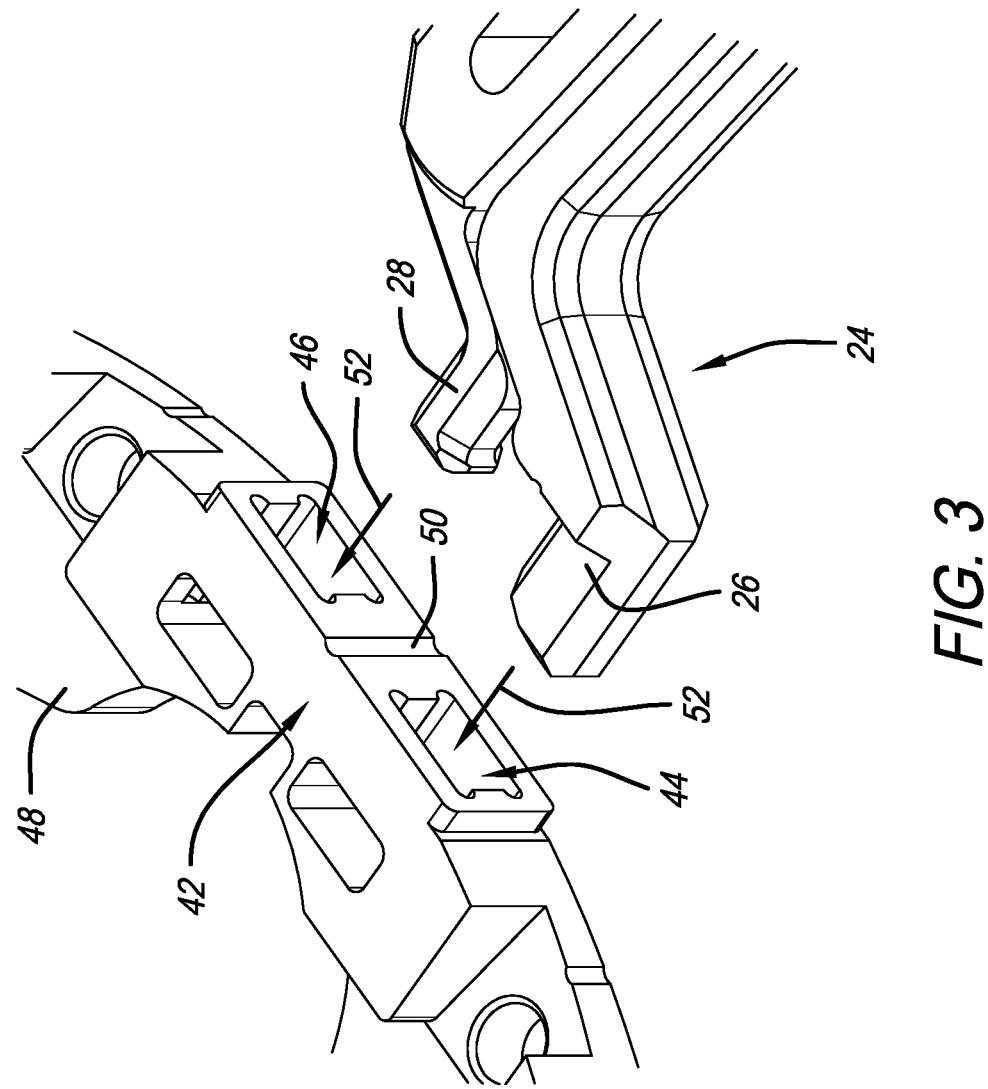
FIG. 3 is an enlarged perspective view similar to FIG. 2, further illustrating alignment of the pair of prongs with a respective pair of reception channels formed within a modular tibial sizer.
Figure 4:
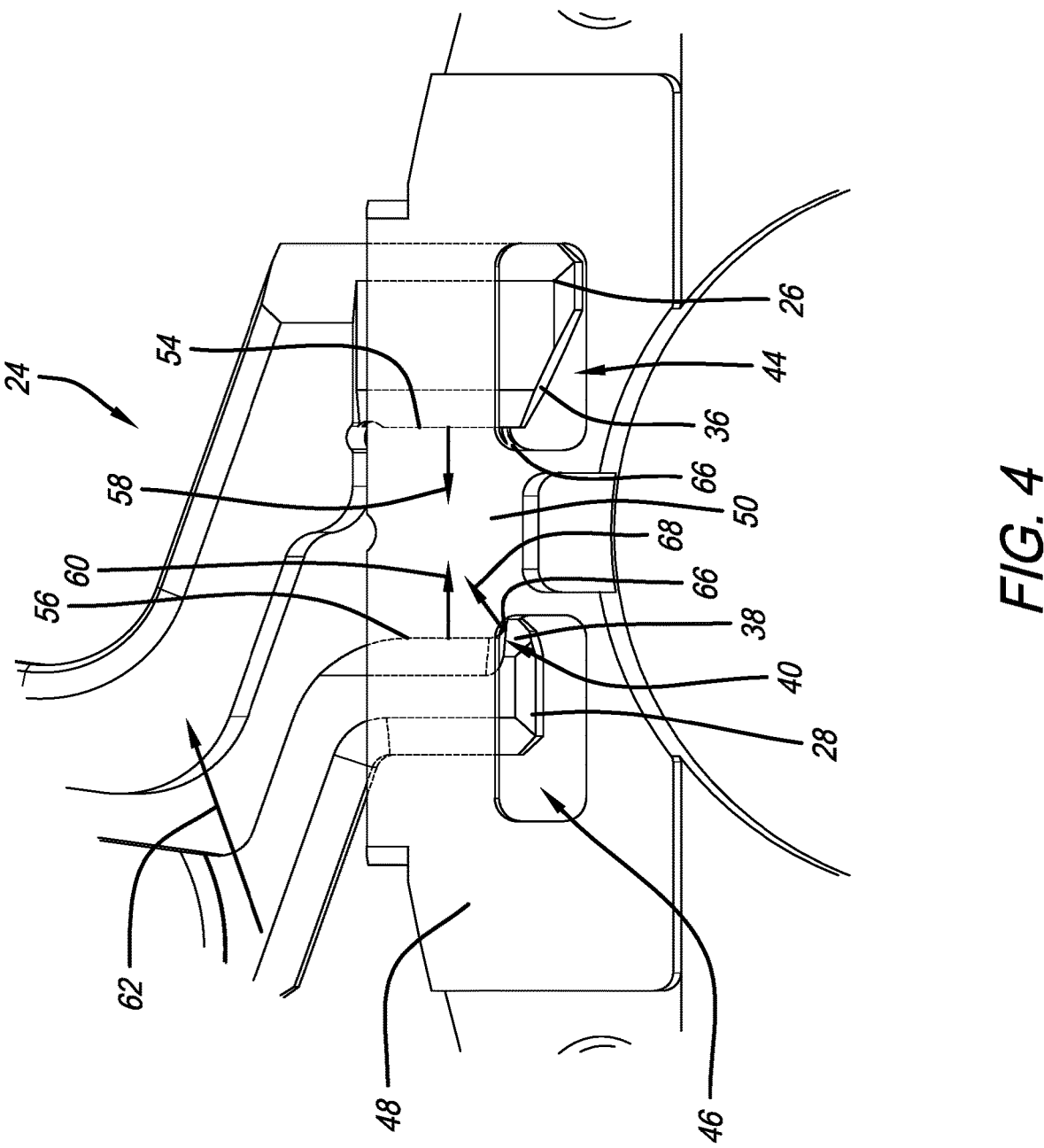
FIG. 4 is a perspective view similar to FIG. 3, further illustrating locking insertion of the pair of prongs within the reception channels of the modular tibial sizer.
Figure 5:
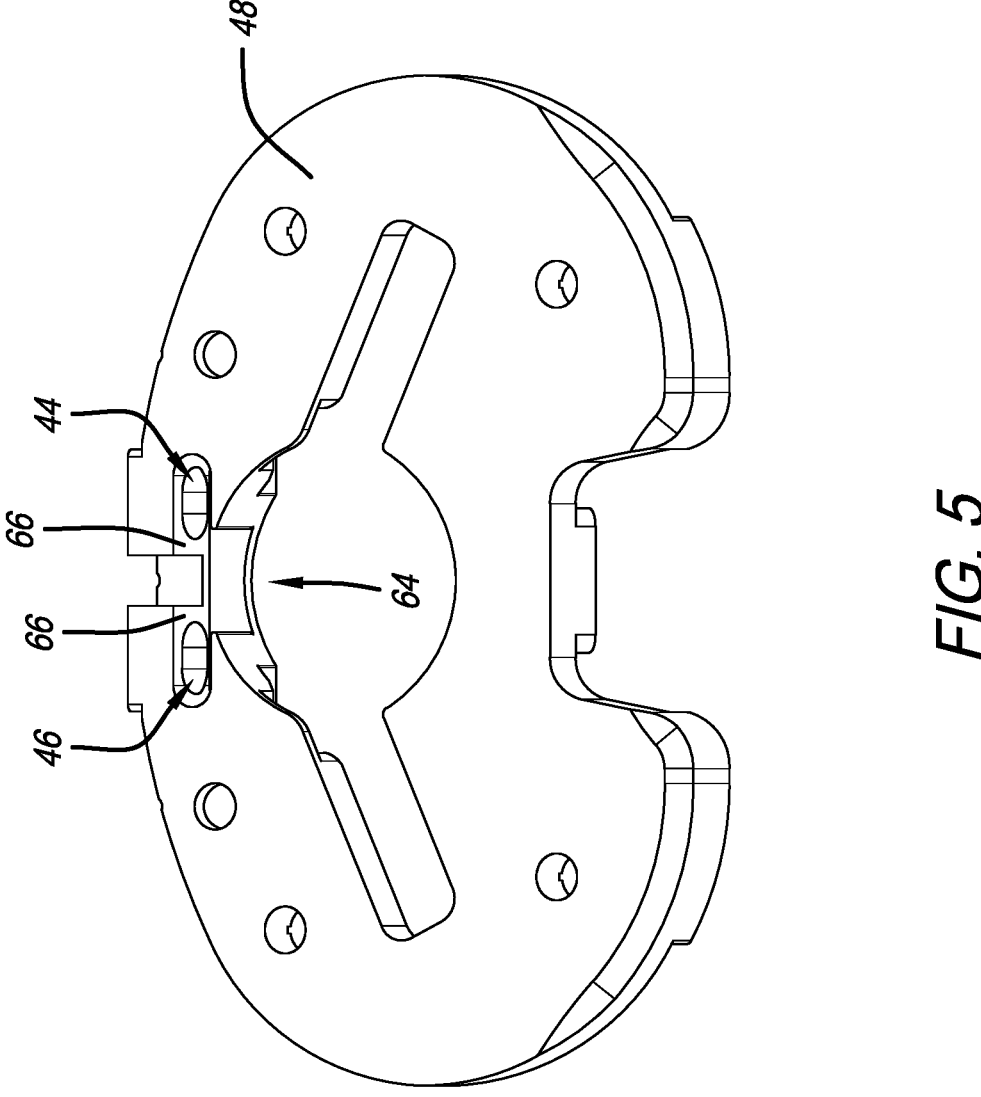
FIG. 5 is a perspective view of the modular tibial sizer, further illustrating the reception channels and a receptive back channel.

As illustrated in FIG. 2, the chamfered prong 26 may be relatively longer than the hooked prong 28 and may include a chamfered leading edge 36. The hooked prong 28 may include a latch 38 generally outwardly projecting into the gap 30 and a trailing notch 40 formed underneath the latch 38 and into a portion of the hooked prong 28 as best illustrated in FIG. 2. As illustrated in FIG. 3, the latching interface 24 including the prongs 26, 28 may generally correspond to a reception interface 42 that may include a first and second reception channel 44, 46. As illustrated in FIGS. 3-5, the reception interface 42 may be located on a modular tibial sizer 48. The reception interface 42 may further include a partition 50 separating the first and second reception channels 44, 46, whereby the gap 30 between the chamfered prong 26 and the hooked prong 28 must be of a sufficient distance to receive the partition 50 therein. In alternative embodiments wherein the latching interface 24 includes three or more prongs, the reception interface 42 may include three or more corresponding reception channels.

As illustrated in FIG. 3, the surgeon may insert the latching interface 24 into the reception interface 42 along arrows 52 so the chamfered prong 26 may engage the reception channel 44 via slide through reception and the hooked prong 28 may engage the reception channel 46 in the same manner. If the prongs 26, 28 are not in the open position, i.e., where the gap 30 is sufficiently wide enough to accept the partition 50 therein, the prongs 26, 28 may contact the partition 50, thereby being prevented from entering the reception channels 44, 46. In this embodiment, the surgeon may need to actuate the hinge 32 via the spring-biased lever arm 34 to open the gap 30 between the prongs 26, 28 by a sufficient distance to facilitate inserting the prongs 26, 28 into the reception channels 44, 46 along arrows 52.

Alternatively, one or both of the prongs 26, 28 may contact a portion of the partition 50, such as along the chamfered leading edge 36 of the chamfered prong 26. Here, the partition 50 may slide along the chamfered leading edge 36 thereby separating the prongs 26, 28 during insertion without the need to actuate the hinge 32 with the spring-biased lever arm 34. In this embodiment, the prongs 26, 28 may essentially self-actuate to a position to be received within each of the reception channels 44, 46 for locking engagement within the reception interface 42.

As best illustrated in FIG. 4, the surgeon may release the spring-biased lever arm 34 after the prongs 26, 28 enter the reception channels 44, 46 for friction fit engagement therein. More specifically, the pretensioned interaction of the spring-biased lever arm 34 relative to the hinge 32 will attempt to return the prongs 26, 28 to the closed position, i.e., closing the gap 30 therebetween. But, since the width of the pre-tensioned gap 30 is relatively smaller than the partition 50, a pair of interior walls 54, 56 of the respective chamfered prong 26 and the hooked prong 28 will contact the partition 50 within the reception channels 44, 46. Because the partition 50 is wider than the pretensions gap 30 while the unibody orthopedic surgical instrument 20 is at rest, the prongs 26, 28 will exert a latching force along directional arrows 58, 60, respectively. As such, and as best illustrated in FIG. 6, this couples the unibody orthopedic surgical instrument 20 to the modular tibial sizer 48 so the surgeon may manipulate and position the modular tibial sizer 48, as needed.

In another embodiment, the chamfered leading edge 36 may contact the partition 50 before the hooked prong 28. As briefly mentioned above, as the chamfered prong 26 slides into the reception channel 44, the chamfered leading edge 36 may cause the prongs 26, 28 to deflect away from one another, thereby widening the gap 30 between the prongs 26, 28. This may also facilitate slide through engagement of the prongs 26, 28 with the reception channels 44, 46 without the need to substantially actuate the hinge 32 via the spring-biased lever arm 34. Furthermore, as best illustrated in FIG. 4, the width of the hooked prong 28 may be relatively smaller than the width of the reception channels 44, 46 and/or the chamfered prong 26. As such, the surgeon may insert the hooked prong 28 at an angle and then pivot the unibody orthopedic surgical instrument 20 in the direction of arrow 62. The chamfered leading edge 36 may then contact the partition 50 and deflect the prongs 26, 28 away from each other to allow the chamfered prong 26 to slide into the reception channel 44. At the very least, the chamfered leading edge 36 deflecting the prongs 26, 28 away from each other may assist the surgeon in inserting the prongs 26, 28 while at the same time actuating the hinge 32 via the spring-biased lever arm 34.

As best illustrated in FIG. 5 with respect to the modular tibial sizer 48, the reception channels 44, 46 may extend into a relatively wider back channel 64. As such, the transition between the relatively narrower reception channels 44, 46 to the wider back channel 64 forms a set of shoulders 66 therebetween. Here, the prongs 26, 28 may extend through the reception channels 44, 46 and into the back channel 64 for engagement with the shoulders 66 to further secure the latching interface 24 to the reception interface 42. As further illustrated in FIG. 4, the hooked prong 28 may extend into the reception channel 44 or 46, and the shoulder 66 may extend into the notch 40. As the notch 40 receives shoulder 66, the latch 38 may extend over and exert a force on the shoulder 66 in the direction of arrow 68 for pull-tight engagement with the modular tibial sizer 48. This may reduce backlash from the modular tibial sizer 48 when coupled to the unibody orthopedic surgical instrument 20 as the modular tibial sizer 48 is pulled towards the unibody orthopedic surgical instrument 20.

Figure 6:
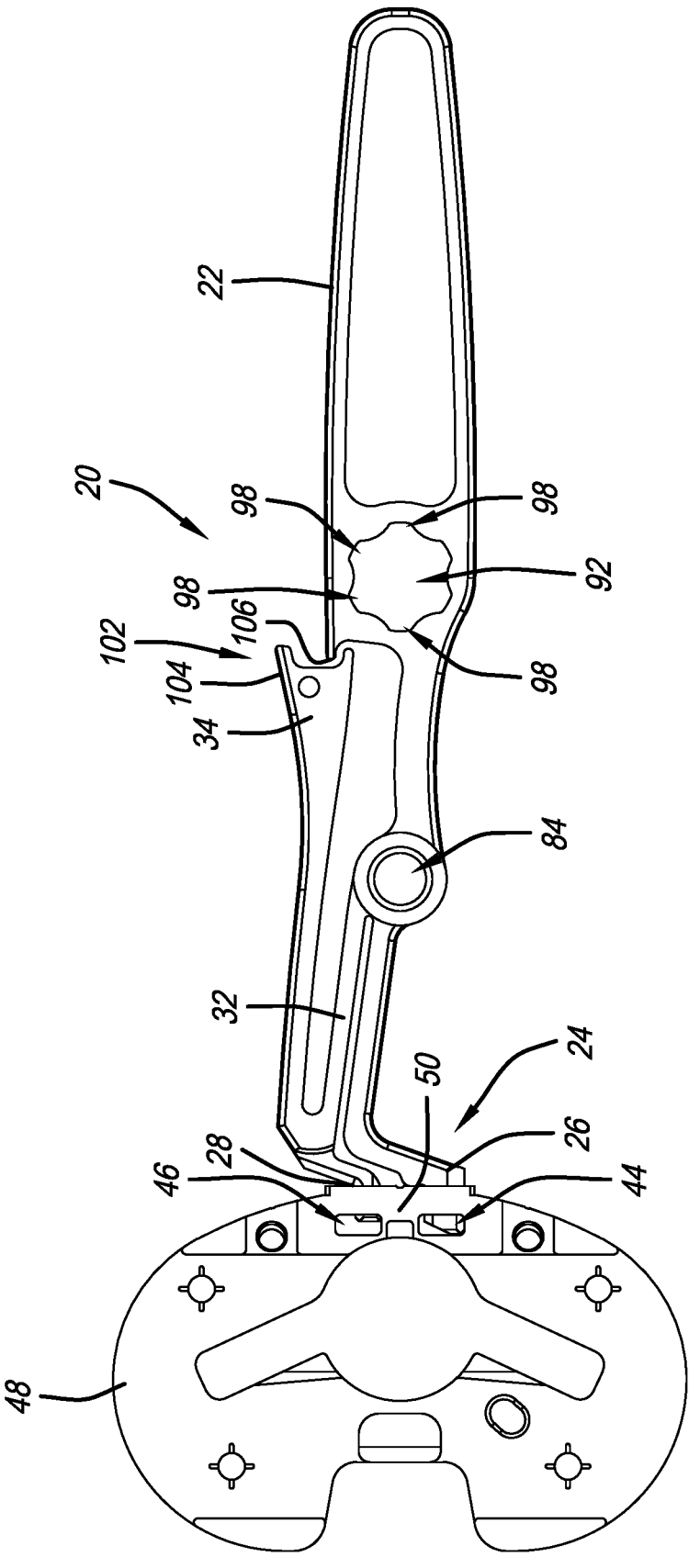
FIG. 6 is a top plan view illustrating the unibody orthopedic surgical instrument with the pair of prongs coupled with the reception channels of the module tibial sizer.

Furthermore, FIG. 6 illustrates the unibody orthopedic surgical instrument 20 coupled to a right-side modular tibial sizer 48 with the chamfered prong 26 engaged with the reception channel 44, and the hooked prong 28 engaged with the reception channel 46. Alternatively, the unibody orthopedic surgical instrument 20 may be flipped over for use with a left-side modular tibial sizer 48 with the chamfered prong 26 engaged with the reception channel 46 and the hooked prong 28 engaged with the reception channel 44. As such, the unibody orthopedic surgical instrument 20 may be used with a knee arthroplasty for both the left and right knee of the patient.

Figure 7:
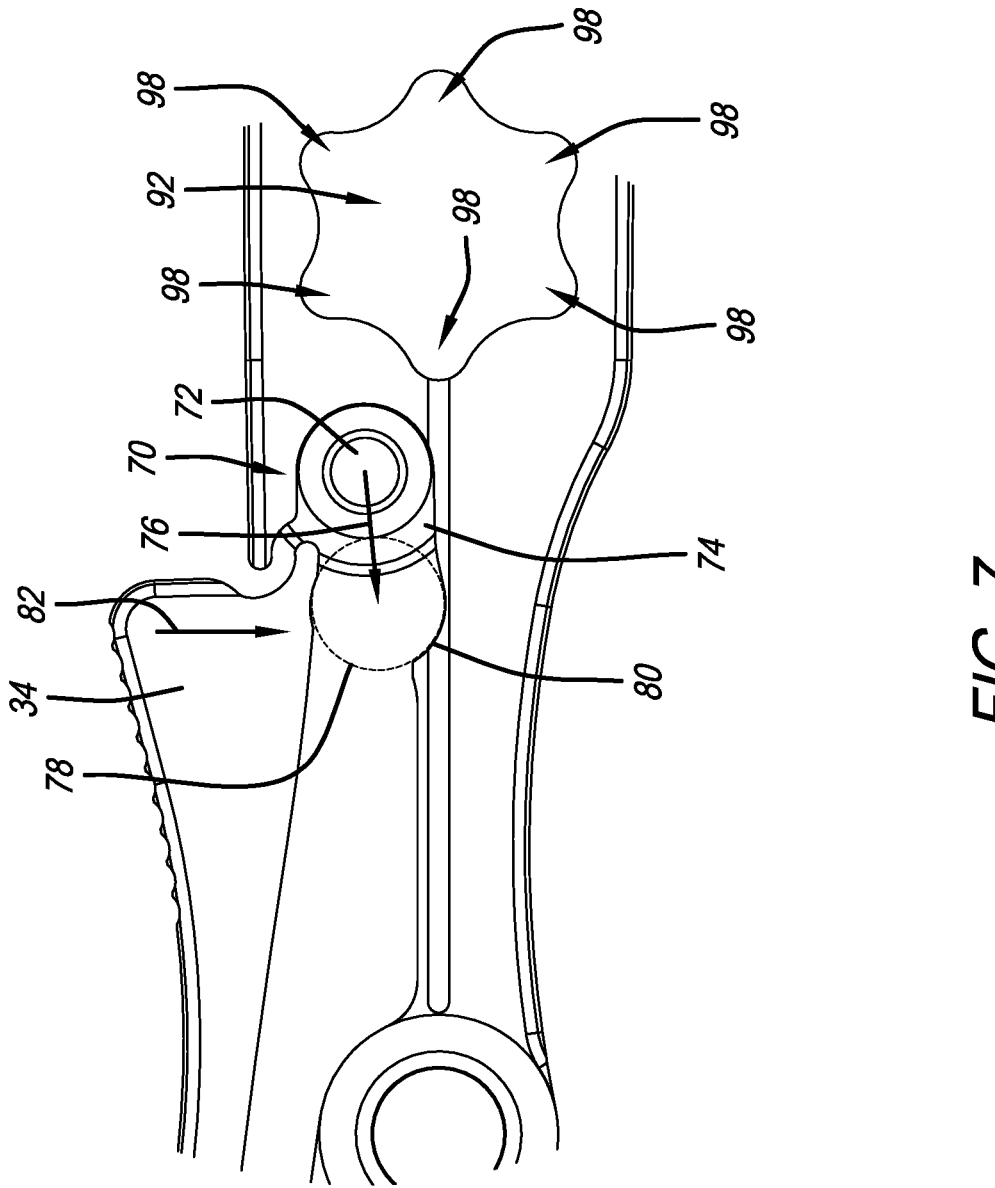
FIG. 7 is an enlarged top plan view taken about the circle 6 in FIG. 1, further illustrating a lock selectively positionable to prevent actuation of a spring-biased lever arm.
Figure 8:
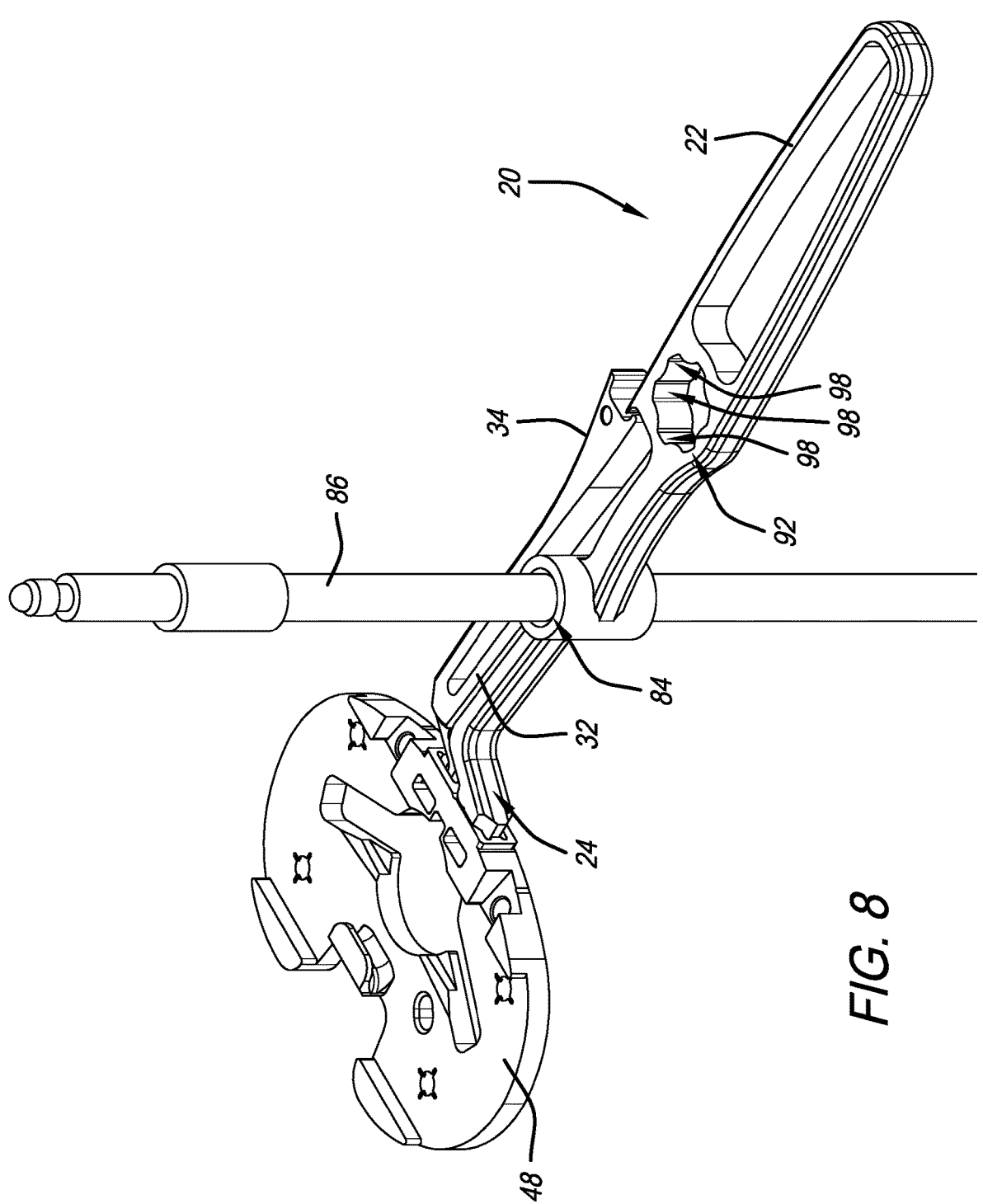
FIG. 8 is a perspective view illustrating the unibody orthopedic surgical instrument engaged with an alignment rod and having the pair of prongs coupled with a tibial trial.
Figure 9:
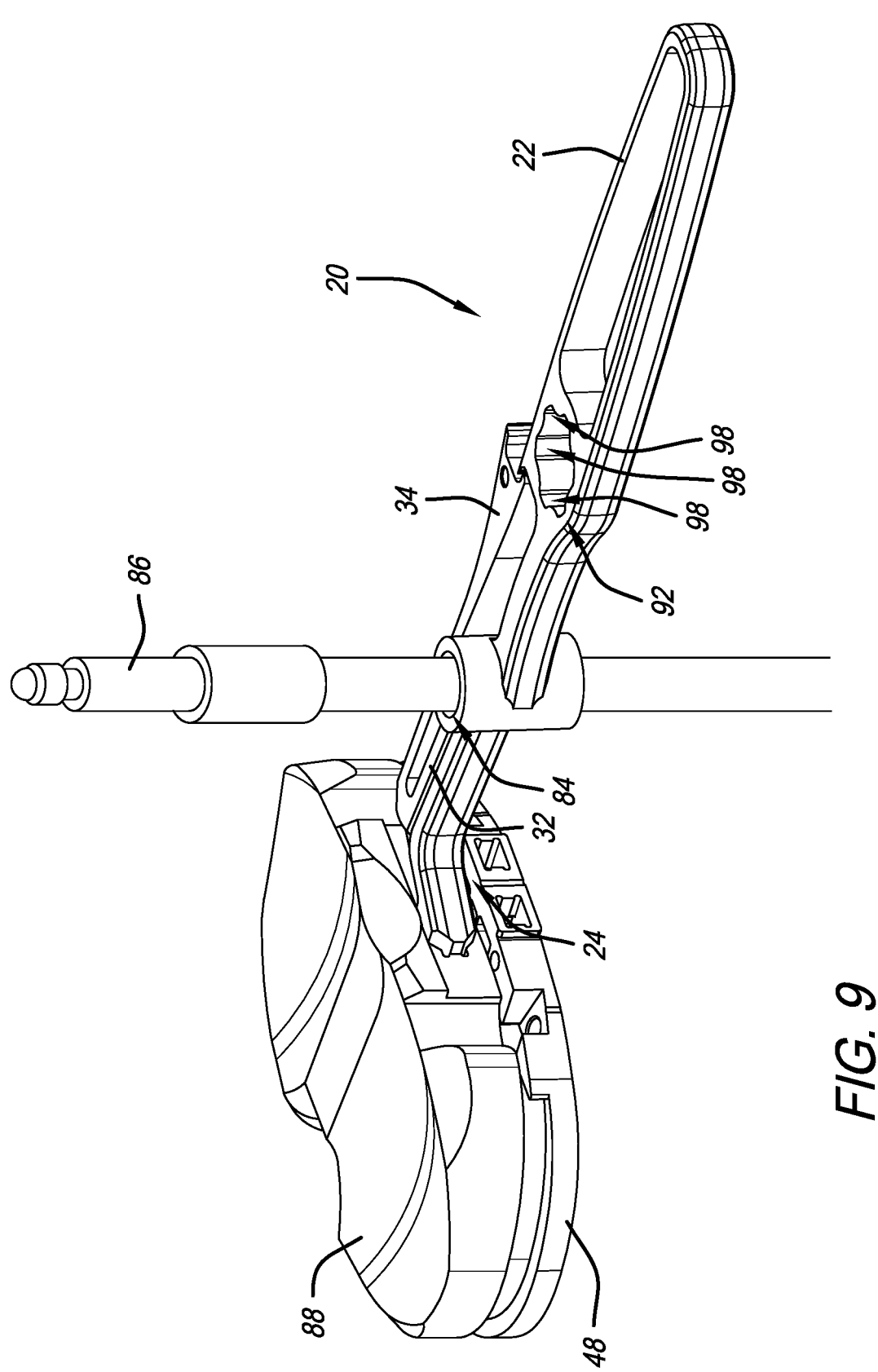
FIG. 9 is a perspective view similar to FIG. 8, further illustrating the unibody orthopedic surgical instrument engaged with the alignment rod and having the pair of prongs coupled with an insert trial.

As illustrated in FIG. 7, the unibody orthopedic surgical instrument 20 may further include a lock 70 having a lock rod 72 and, as best illustrated in FIG. 1, a pair of opposing end caps 74 (one illustrated in FIG. 7 and two illustrated in FIG. 1) outwardly extending from each end of the lock rod 72. In this respect, the end caps 74 may be of a sufficient diameter or width to at least partially extend out over each side of the unibody orthopedic surgical instrument 20 to maintain the lock 70 in an engaged relationship with the integrated handle 22. The surgeon may slide the lock 70 along an arrow 76 from an unlocked position illustrated in FIG. 7 immediately below the spring-biased lever arm 34 to a locked position wherein the lock 70 is positioned immediately behind the spring-biased lever arm 34 as indicated in dotted line depiction 78 in FIG. 7. When in the locked position, the lock 70 may seat against an inwardly projecting curved member 80 that prevents the lock 70 from continuing too far past the locked position, and also biases the lock 70 into positive engagement with the spring-biased lever arm 34. As such, when the lock 70 is in the locked position, the lock rod 72 prevents the spring-biased lever arm 34 from being depressed inwardly along directional arrow 82, thereby effectively preventing actuation of the hinge 32 and the resultant widening of the gap 30 between the prongs 26, 28. The lock 70 may be particularly useful when the unibody orthopedic surgical instrument 20 is used to align an insert trial. For example, the insert trial must be inserted into a gap between the tibial component and femoral component. This typically requires a significant amount of force. As such, the lock 70 may ensure that the force exerted on the insert trial does not cause disengagement of the prongs 26, 28 from the insert trial as a result of forcibly gripping the integrated handle 22, including, e.g., the spring-biased lever arm 34. Therefore, it follows that the lock 70 further ensures that the surgeon does not accidentally actuate the hinge 32.

Figure 10:
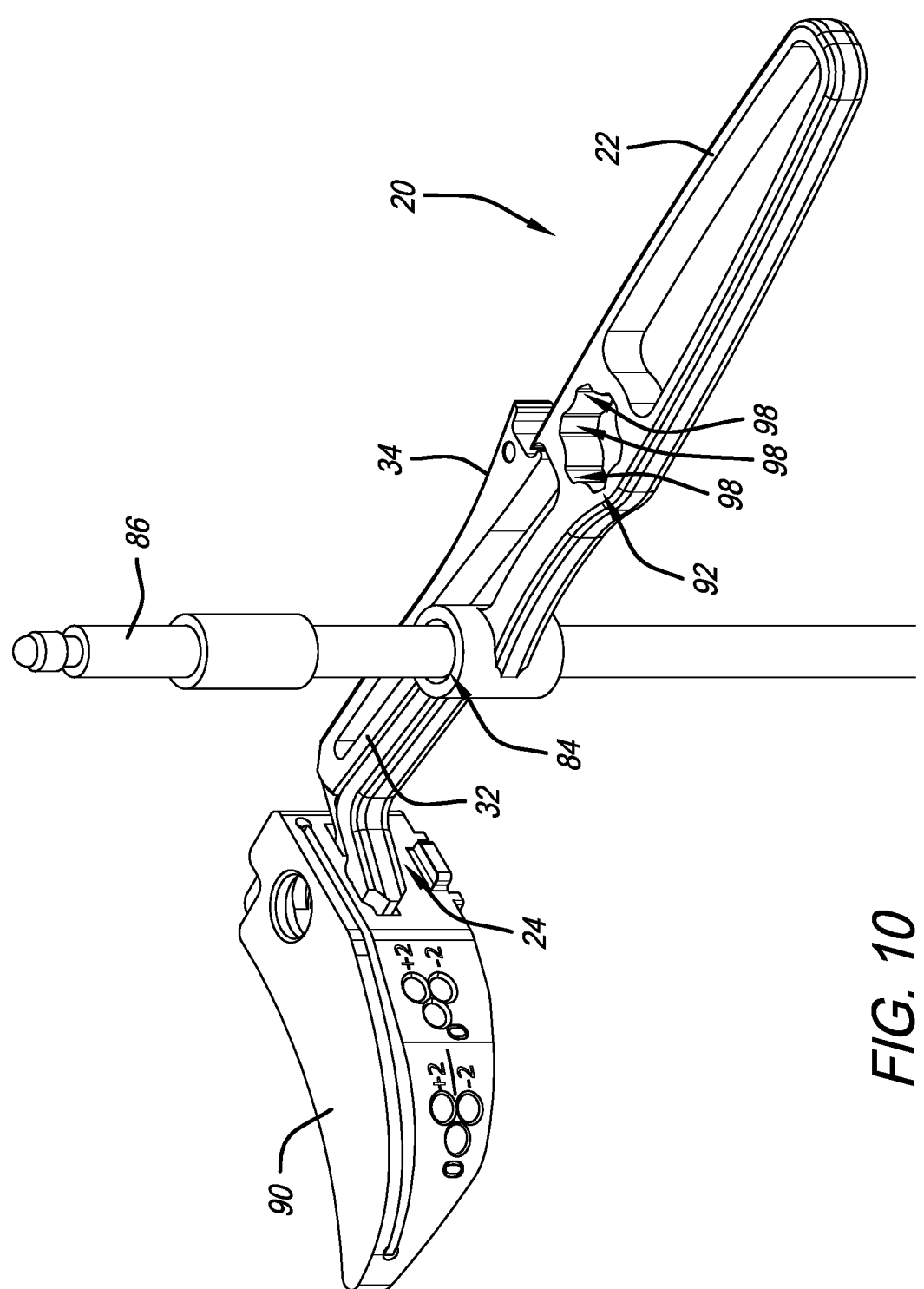
FIG. 10 is a perspective view similar to FIGS. 8 and 9, additionally illustrating the unibody orthopedic surgical instrument engaged with the alignment rod and having the pair of prongs coupled with a tibial cutting guide.

As illustrated in FIGS. 1, 6, and 8-12, the unibody orthopedic surgical instrument 20 may include an alignment rod aperture 84 for slidable engagement with an alignment rod 86. Furthermore, the unibody orthopedic surgical instrument 20 may serve as an indicator of rotation, thus improving alignment. The unibody orthopedic surgical instrument 20 may slide along the length of the alignment rod 86 wherein the surgeon may use a lock (not shown) to secure the unibody orthopedic surgical instrument 20 to a desired location along the length of the alignment rod 86. The unibody orthopedic surgical instrument 20 may rotate around the alignment rod 86 about the alignment rod aperture 84. Moreover, as further illustrated in FIGS. 8-11, the latching interface 24 may couple a plurality of knee replacement components and instruments such as the modular tibial sizer 48 (FIG. 8), an insert trial 88 (FIG. 9), and/or a tibial cutting guide 90 (FIG. 10). As such, the insert trial 88 and the tibial cutting guide 90 may include the same or similar reception interface 42 as the modular tibial sizer 48 disclosed above.

Figure 11:
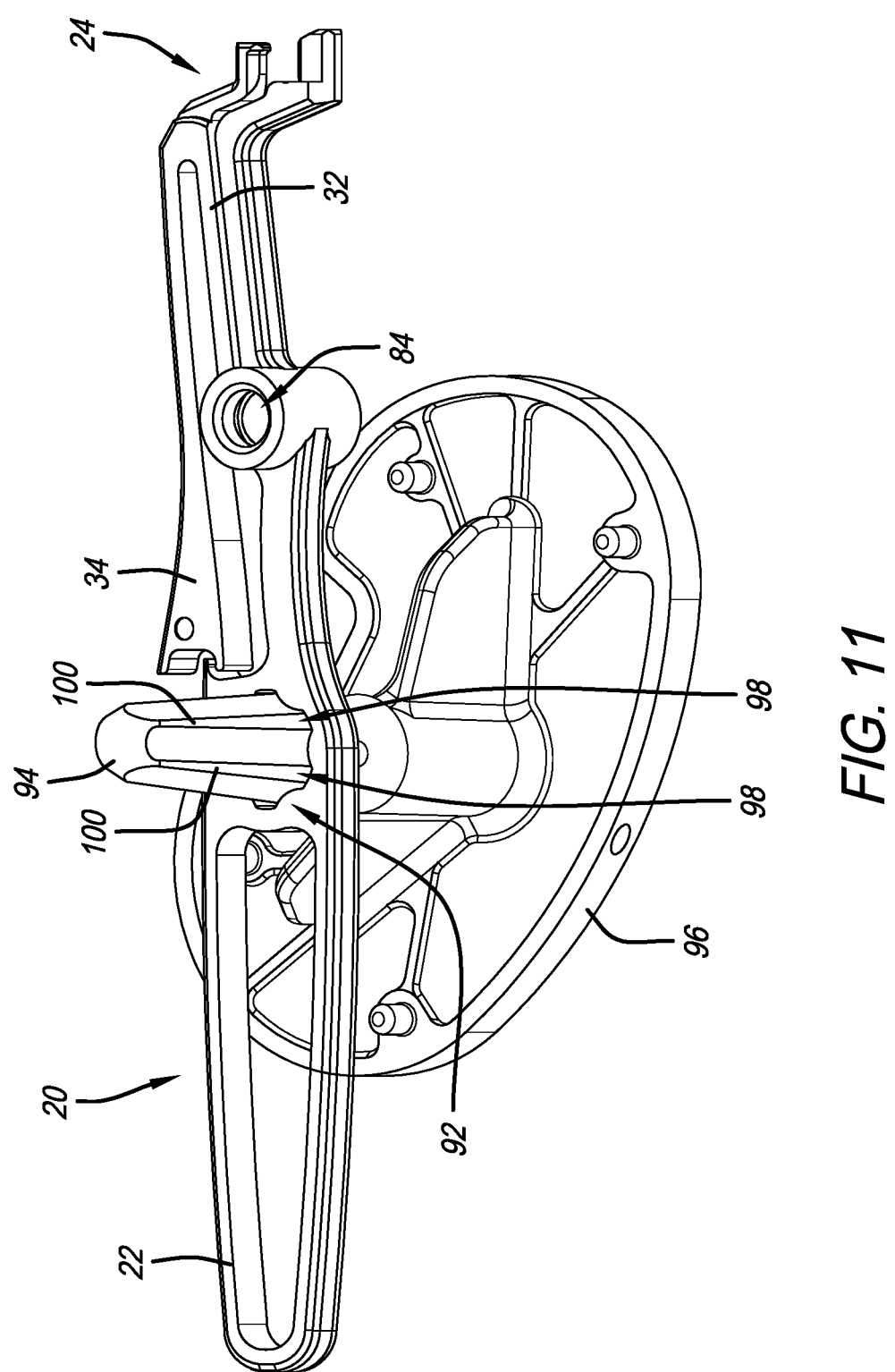
FIG. 11 is a perspective view the unibody orthopedic surgical instrument with a body-integrated stem wrench engaged with a tibial baseplate stem.

As illustrated in FIG. 11, the unibody orthopedic surgical device 20 may include a tibial stem wrench 92 that may couple to a tibial stem 94 on a tibial baseplate 96. The surgeon may rotate the tibial stem wrench 92 about the tibial stem 94 to extend or shorten the tibial stem 94. In one embodiment, the tibial stem wrench 92 may include a series of indentations 98 that correspond to a set of ribs 100 on the tibial stem 94. The indentations 98 may prevent the tibial stem wrench 92 from slipping or concentrically rotating around the tibial stem 94 instead of turning the tibial stem 94.

More specifically with respect to the operation of the hinge 32, the top plan view of FIG. 6 best illustrates that the spring-biased lever arm 34 includes an actuation end 102 that terminates in a U- or C-shaped channel 104 that generally encompasses and floats within an end stop 106 generally projecting outwardly from a portion of the integrated handle 22 and into the C-shaped channel 104. As such, the spring-biased lever arm 34 may only deflect by a distance of the open enclosure formed within the C-shaped channel 104 around the end stop 106. In other words, the outwardly projecting end stop 106 prevents the spring-biased lever arm 34 from deflecting an undesirable distance by way of projecting into and contacting opposite sides of the C-shaped channel 104, as needed. Such feature prevents over extension of the hinge 32 while at the same time maintaining the location of the spring-biased lever arm 34 in a generally lengthwise relationship with the integrated handle 22.

Moreover, as also illustrated in FIG. 6, the spring-biased lever arm 34 is generally elongated and curves about itself into the hinge 32 carrying, at least in this embodiment, the hooked prong 28. As shown, the hinge 32 extends back about the length of the spring-biased lever arm 34 in spaced apart relation relative thereto and couples with the alignment rod aperture 84. The hinge 32 is also illustrated in FIG. 6 being in spaced apart relation relative to the chamfered prong 26 positioned immediately below, which also couples with the alignment rod aperture 84. As such, compression of the spring-biased lever arm 34 into the body of the integrated handle 22 exerts a force on the curvature where the spring-biased lever arm 34 transitions or curves back into the hinge 32, thereby causing the hinge 32 to pull or retract away from the chamfered prong 26 about its connection to the alignment aperture 84. The same or greater movement may be experienced where the hinge 32 couples to or otherwise pivots relative to the handle 22, such as the part of the handle 22 forming the alignment rod aperture 84. Such movement increases the width of the gap 30 between each of the chamfered prong 26 and the hooked prong 28. This, in turn, provides the necessary clearance for inserting and/or removing each of the chamfered prong 26 and the hooked prong 28 into the respective reception channels 44, 46, as discussed above. Releasing the spring-biased lever arm 34 returns the hinge 32 back to a substantial parallel relation with the chamfered prong 26 to facilitate engagement of the unibody orthopedic surgical instrument 20 with the modular tibial sizer 48, as discussed herein. The unibody orthopedic surgical instrument 20 may be prefabricated such that the spring biased lever arm 34 and the hinge 32 are pretensioned relative to the chamfered prong 26 so that the gap 30 is somewhat smaller than the partition 50, which facilitates engagement between the latching interface 24 and the reception interface 42 as discussed above.

Figure 12:
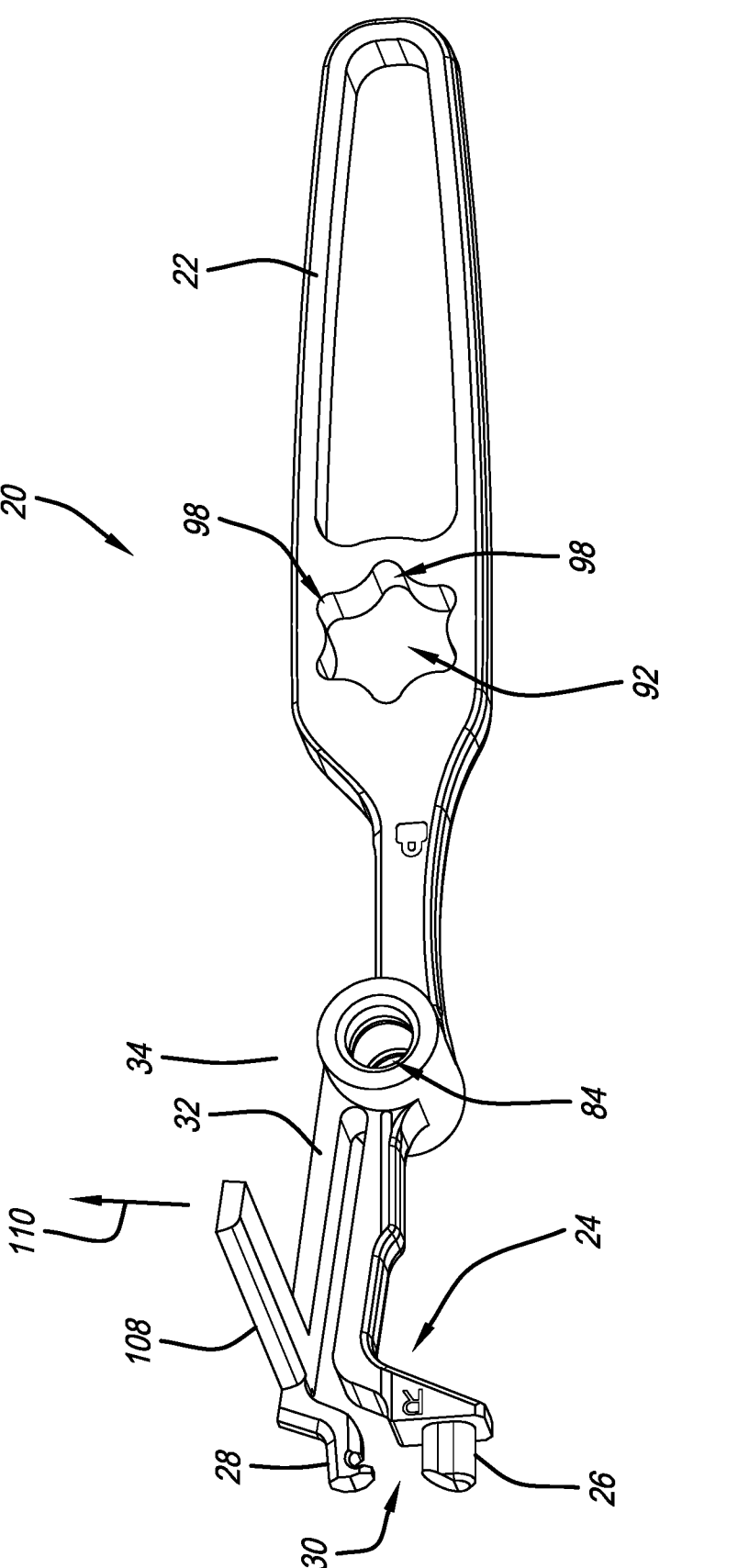
FIG. 12 is a perspective view of an alternative embodiment of the unibody orthopedic surgical instrument illustrating an orthogonal lever arm selectively operable with a hinge to actuate the pair of prongs.

Another alternative embodiment of the unibody orthopedic surgical instrument 20 is illustrated in FIG. 12 with respect to an orthogonal lever arm 108 outwardly extending from a portion of the hinge 32. The orthogonal lever arm 108 is able to selectively actuate the hinge 32 by applying an upward or downward force along directional arrow 110 to govern the width of the gap 30 between the chamfered prong 26 and the hooked prong 28. In operation, e.g., the surgeon may hold the unibody orthopedic surgical instrument 20 by the handle 22 with one hand and use another hand to apply a force to the orthogonal lever arm 108 along the direction of arrow 110. Applying the force along the directional arrow 110 in an upward or clockwise manner as illustrated in FIG. 12 causes the hooked prong 28 to defect up and away from the chamfered prong 26, thereby increasing the gap 30 in between. This facilitates disengagement of the latching interface 24 from the reception interface 42, as discussed above in detail.

In alternative embodiments, the orthogonal lever arm 108 could also be pinched or pulled to apply the force along the directional arrow 110 to accomplish increasing or decreasing the gap 30 between the chamfered prong 26 and the hooked prong 28. Additionally, applying the force in an opposite direction of the arrow 110 would naturally create the opposite effect, e.g., decreasing the gap 30 between the chamfered prong 26 and the hooked prong 28 as per the embodiment illustrated in FIG. 12. While FIG. 12 illustrates the orthogonal lever arm 108 and the hinge 32 operably coupled to the hooked prong 28, the orthogonal lever arm 108 and the hinge 32 could also be operably coupled with the chamfered prong 26 in the alternative. Although, regardless of the orientation, coupling, and/or the direction of the force applied thereto, the orthogonal lever arm 108 is able to effectuate actuations of the hinge 32 for purposes of moving the hooked prong 28 relative to the chamfered prong 26 to either increase or decrease the gap 30 in between, as may be desired.

Similar to that discussed above in detail with respect to FIGS. 3-4, once the prongs 26, 28 are inserted into the reception channels 44, 46, release of the orthogonal lever arm 108 should cause the hinge 32 to return the prongs 26, 28 to the closed or locked position, thereby applying a latching force to the partition 50 to maintain the latching interface 24 in coupled arrangement with the reception interface 42.

Alternatively, the unibody orthopedic surgical instrument 20 may include a commensurate orthogonal lever arm (not shown) extending away from the opposite side of the unibody orthopedic surgical instrument 20, thereby allowing the unibody orthopedic surgical instrument 20 to be flipped over and used with a knee arthroplasty for both the left and right knee of the patient. While FIG. 12 illustrates the orthogonal lever arm 108 generally extending perpendicular to the unibody orthopedic surgical instrument 20, in alternative embodiments, the orthogonal lever arm 108 may extend away from the unibody orthopedic surgical instrument at any angle, or generally parallel to the unibody orthopedic surgical instrument.

Although several embodiments have been described in detail for purposes of illustration, various modifications may be made without departing from the scope and spirit of the invention. Accordingly, the invention is not to be limited, except as by the appended claims.

What is claimed is:

1. A unibody orthopedic instrument, comprising:
an elongated handle;
a latching interface outwardly extending relative to the elongated handle and selectively couplable to an orthopedic component; and
a hand accessible spring-biased lever arm operable with a hinge coupled to the elongated handle about a pivot, the hinge normally positioning the latching interface in a first latched position for locking engagement with the orthopedic component and being operable by the spring-biased lever arm about the pivot to reposition the latching interface from the normally latched position to an unlatched position for disengagement from the orthopedic component;
wherein the spring-biased lever arm terminates in a C-shaped enclosure generally encompassing an end stop outwardly projecting from the elongated handle, the spring-biased lever arm deflectable relative to the elongated handle by a distance formed between opposing sides of the C-shaped channel.

2. The orthopedic instrument of claim 1, wherein the spring-biased lever arm turns about and extends away from the hinge in an offset position relative thereto.

3. The orthopedic instrument of claim 1, wherein the latching interface includes a pair of pretensioned prongs positioned relatively closer to one another when in the latched position than when in the unlatched position.

4. The orthopedic instrument of claim 3, wherein one of the pair of pretensioned prongs includes a chamfered prong having a chamfered leading edge and the other of the pair of pretensions-pretensioned prongs includes a hooked prong having a notch formed thereunder.

5. The orthopedic instrument of claim 1, wherein the latching interface comprises a size and shape for select slide-in reception within a pair of receptors integrated into the orthopedic component for locking engagement therewith.

6. The orthopedic instrument of claim 1, including a lock movable relative to an operable end of the spring-biased lever arm between an unlocked position allowing the movement of the operable end of the spring-biased lever arm and a locked position obstructing movement of the operable end of the spring-biased lever arm.

7. The orthopedic instrument of claim 6, wherein the lock comprises a rod movable within a channel separating the operable end of the spring-biased lever arm and the elongated body between the unlocked position and the locked position.

8. The orthopedic instrument of claim 7, wherein the elongated handle includes a stop projecting into the channel to locate the lock underneath the spring-biased lever arm in the locked position.

9. The orthopedic instrument of claim 1, wherein the elongated handle includes an aperture having a size and shape for select sliding engagement with an alignment rod.

10. The orthopedic instrument of claim 1, wherein the elongated handle further includes a body-integrated tibial stem wrench.

11. A unibody orthopedic instrument, comprising:
a handle;
a latching interface outwardly extending relative to the handle and selectively couplable to an orthopedic component;

a spring-biased lever arm integrated with a hinge coupled to the handle about a pivot normally positioning the latching interface in a first latched position for locking engagement with the orthopedic component and being operable by the spring-biased lever arm about the pivot to reposition the latching interface from the normally latched position to an unlatched position for disengagement from the orthopedic component; and
a lock movable relative to the spring-biased lever arm between an unlocked position allowing movement of the spring-biased lever arm and a locked position obstructing movement of the spring-biased lever arm;
wherein the lock comprises a rod movable within a channel separating an operable end of the spring-biased lever arm and the handle, the rod being in the locked position underneath at least a portion of the operable end of the spring-biased lever arm adjacent a stop projecting into the channel.

12. The orthopedic instrument of claim 11, wherein the latching interface includes a pair of pretensioned prongs positioned relatively closer to one another when in the latched position than when in the unlatched position, the pair of pretensioned prongs comprising a size and shape for select slide-in reception within a pair of receptors integrated into the orthopedic component for locking engagement therewith.

13. The orthopedic instrument of claim 12, wherein one of the pair of pretensioned prongs includes a chamfered prong having a chamfered leading edge and the other of the pair of pretensioned prongs includes a hooked prong having a notch formed thereunder.

14. The orthopedic instrument of claim 11, wherein the spring-biased lever arm terminates in a C-shaped enclosure generally encompassing at least a portion of the handle.

15. The orthopedic instrument of claim 11, wherein the handle includes an aperture having a size and shape for select sliding engagement with an alignment rod and a body-integrated tibial stem wrench.

16. The orthopedic instrument of claim 11, wherein the spring-biased lever arm turns about and extends over the hinge in spaced-apart relation.

17. A unibody orthopedic instrument, comprising:
an elongated handle;
a latching interface outwardly extending relative to the elongated handle and selectively couplable to an orthopedic component, wherein the latching interface includes a pair of pretensioned prongs positioned relatively closer to one another when in the latched position than when in the unlatched position; and
a hand accessible spring-biased lever arm operable with a hinge coupled to the elongated handle about a pivot, the hinge normally positioning the latching interface in a first latched position for locking engagement with the orthopedic component and being operable by the spring-biased lever arm about the pivot to reposition the latching interface from the normally latched position to an unlatched position for disengagement from the orthopedic component, wherein one of the pair of pretensioned prongs includes a chamfered prong having a chamfered leading edge and the other of the pair of pretensioned prongs includes a hooked prong having a notch formed thereunder.

18. A unibody orthopedic instrument, comprising:
an elongated handle;
a latching interface outwardly extending relative to the elongated handle and selectively couplable to an orthopedic component;

a hand accessible spring-biased lever arm operable with a hinge coupled to the elongated handle about a pivot, the hinge normally positioning the latching interface in a first latched position for locking engagement with the orthopedic component and being operable by the spring-biased lever arm about the pivot to reposition the latching interface from the normally latched position to an unlatched position for disengagement from the orthopedic component; and a lock movable relative to an operable end of the spring-biased lever arm between an unlocked position allowing movement of the operable end of the spring-biased lever arm and a locked position obstructing movement of the operable end of the spring-biased lever arm, wherein the lock comprises a rod movable within a channel separating the operable end of the spring-biased lever arm and the elongated body between the unlocked position and the locked position.

19. A unibody orthopedic instrument, comprising:

an elongated handle including a body-integrated tibial stem wrench;

a latching interface outwardly extending relative to the elongated handle and selectively couplable to an orthopedic component; and a hand accessible spring-biased lever arm operable with a hinge coupled to the elongated handle about a pivot, the hinge normally positioning the latching interface in a first latched position for locking engagement with the orthopedic component and being operable by the spring-biased lever arm about the pivot to reposition the latching interface from the normally latched position to an unlatched position for disengagement from the orthopedic component.

20. The orthopedic instrument of claim 19, wherein the spring-based lever arm orthogonally extends our and away from the hinge.

21. A unibody orthopedic instrument, comprising:

a handle;

a latching interface outwardly extending relative to the handle and selectively couplable to an orthopedic component;

a spring-biased lever arm integrated with a hinge coupled to the handle about a pivot normally positioning the latching interface in a first latched position for locking engagement with the orthopedic component and being operable by the spring-biased lever arm about the pivot to reposition the latching interface from the normally latched position to an unlatched position for disengagement from the orthopedic component; and a lock movable relative to the spring-biased lever arm between an unlocked position allowing movement of the spring-biased lever arm and a locked position obstructing movement of the spring-biased lever arm;

wherein the latching interface includes a pair of pretensioned prongs positioned relatively closer to one another when in the latched position than when in the unlatched position, the pair of pretensioned prongs comprising a size and shape for select slide-in reception within a pair of receptors integrated into the orthopedic component for locking engagement therewith;

wherein one of the pair of pretensioned prongs includes a chamfered prong having a chamfered leading edge and the other of the pair of pretensioned prongs includes a hooked prong having a notch formed thereunder.

22. A unibody orthopedic instrument, comprising:

a handle;

a latching interface outwardly extending relative to the handle and selectively couplable to an orthopedic component;

a spring-biased lever arm integrated with a hinge coupled to the handle about a pivot normally positioning the latching interface in a first latched position for locking engagement with the orthopedic component and being operable by the spring-biased lever arm about the pivot to reposition the latching interface from the normally latched position to an unlatched position for disengagement from the orthopedic component, wherein the spring-biased lever arm terminates in a C-shaped enclosure generally encompassing at least a portion of the handle; and a lock movable relative to the spring-biased lever arm between an unlocked position allowing movement of the spring-biased lever arm and a locked position obstructing movement of the spring-biased lever arm.

23. A unibody orthopedic instrument, comprising:

a handle including an aperture having a size and shape for select sliding engagement with an alignment rod or a body-integrated tibial stem wrench;

a latching interface outwardly extending relative to the handle and selectively couplable to an orthopedic component;

a spring-biased lever arm integrated with a hinge coupled to the handle about a pivot normally positioning the latching interface in a first latched position for locking engagement with the orthopedic component and being operable by the spring-biased lever arm about the pivot to reposition the latching interface from the normally latched position to an unlatched position for disengagement from the orthopedic component; and a lock movable relative to the spring-biased lever arm between an unlocked position allowing movement of the spring-biased lever arm and a locked position obstructing movement of the spring-biased lever arm.

24. A unibody orthopedic instrument, comprising:

a handle;

a latching interface outwardly extending relative to the handle and selectively couplable to an orthopedic component;

a spring-biased lever arm integrated with a hinge coupled to the handle about a pivot normally positioning the latching interface in a first latched position for locking engagement with the orthopedic component and being operable by the spring-biased lever arm about the pivot to reposition the latching interface from the normally latched position to an unlatched position for disengagement from the orthopedic component, wherein the spring-biased lever arm turns about and extends over the hinge in spaced-apart relation; and a lock movable relative to the spring-biased lever arm between an unlocked position allowing movement of the spring-biased lever arm and a locked position obstructing movement of the spring-biased lever arm.

* * * * *